United States Patent
Tatzel et al.

(10) Patent No.: US 12,179,283 B2
(45) Date of Patent: Dec. 31, 2024

(54) METHOD FOR EVALUATING A LASER CUT EDGE, MOBILE TERMINAL AND SYSTEM

(71) Applicant: TRUMPF Werkzeugmaschinen GmbH + Co. KG, Ditzingen (DE)

(72) Inventors: Leonie Felica Tatzel, Korntal (DE); Manuel Kiefer, Sinsheim (DE); Jens Ottnad, Karlsruhe (DE)

(73) Assignee: TRUMPF WERKZEUGMASCHINEN SE + CO. KG, Ditzingen (DE)

( * ) Notice: Subject to any disclaimer, the term of this patent is extended or adjusted under 35 U.S.C. 154(b) by 413 days.

(21) Appl. No.: 17/553,872

(22) Filed: Dec. 17, 2021

(65) Prior Publication Data
US 2022/0105590 A1     Apr. 7, 2022

Related U.S. Application Data (63) Continuation of application No. PCT/EP2020/063545, filed on May 14, 2020.

(30) Foreign Application Priority Data

Jun. 24, 2019   (DE) ................... 102019209088.5

(51) Int. Cl.
  *B23K 26/03*    (2006.01)
  *B23K 26/12*    (2014.01)
  (Continued)

(52) U.S. Cl.
  CPC .......... *B23K 26/032* (2013.01); *B23K 26/123* (2013.01); *B23K 26/1437* (2015.10);
  (Continued)

(58) Field of Classification Search
  CPC ............ G06N 20/00; G06N 3/02; G06N 3/08; G06N 3/088; G06N 3/084; G06N 3/045;
  (Continued)

(56) References Cited

U.S. PATENT DOCUMENTS

| 10,339,655 B2 | 7/2019 | Jerebko et al. |
| 2003/0120714 A1 | 6/2003 | Wolff et al. |

(Continued)

FOREIGN PATENT DOCUMENTS

| CN | 105144241 A | 12/2015 |
| CN | 204997230 U | 1/2016 |

(Continued)

OTHER PUBLICATIONS

Search Machine translation of CN 105787930 A to Zhai et al., Based on Saliency Detection Method and System for Blurring of Image Sharpness, translated Mar. 21, 2024, 16 pages. (Year: 2024).*

(Continued)

*Primary Examiner* — Matthew C Bella
*Assistant Examiner* — Dennis Rosario
(74) *Attorney, Agent, or Firm* — LEYDIG, VOIT & MAYER, LTD.

(57) ABSTRACT

A method for evaluating a laser cut edge of a workpiece includes capturing image data of the laser cut edge and its surroundings, segmenting the image data, and identifying a segment of interest of the image data. The segment of interest comprises image data of the laser cut edge. The method further includes carrying out an image quality detection for the segment of interest and generating, based on the image quality detection, an output for a user.

13 Claims, 6 Drawing Sheets

(51) Int. Cl.

| | |
|---|---|
| *B23K 26/14* | (2014.01) |
| *B23K 31/12* | (2006.01) |
| *G06F 3/01* | (2006.01) |
| *G06F 3/048* | (2013.01) |
| *G06F 3/04847* | (2022.01) |
| *G06F 3/14* | (2006.01) |
| *G06T 5/73* | (2024.01) |
| *G06T 7/00* | (2017.01) |
| *G06T 7/10* | (2017.01) |
| *G06T 7/11* | (2017.01) |
| *G06T 7/12* | (2017.01) |
| *G06V 10/25* | (2022.01) |
| *G06V 10/26* | (2022.01) |
| *H04N 21/485* | (2011.01) |
| *H04N 23/62* | (2023.01) |
| *H04N 23/67* | (2023.01) |
| *A61F 9/008* | (2006.01) |
| *B23K 26/142* | (2014.01) |
| *B23K 26/38* | (2014.01) |
| *B23K 101/18* | (2006.01) |

(52) U.S. Cl.
CPC .............. *B23K 31/125* (2013.01); *G06F 3/01* (2013.01); *G06F 3/048* (2013.01); *G06F 3/04847* (2013.01); *G06F 3/14* (2013.01); *G06T 5/73* (2024.01); *G06T 7/0002* (2013.01); *G06T 7/0004* (2013.01); *G06T 7/10* (2017.01); *G06T 7/11* (2017.01); *G06T 7/12* (2017.01); *G06V 10/25* (2022.01); *G06V 10/26* (2022.01); *H04N 21/4854* (2013.01); *H04N 23/62* (2023.01); *H04N 23/675* (2023.01); *A61F 9/00814* (2013.01); *B23K 26/142* (2015.10); *B23K 26/38* (2013.01); *B23K 2101/18* (2018.08); *G05B 2219/36199* (2013.01); *G05B 2219/40613* (2013.01); *G05B 2219/45041* (2013.01); *G05B 2219/45165* (2013.01); *G05B 2219/49353* (2013.01); *G06T 2200/24* (2013.01); *G06T 2207/10148* (2013.01); *G06T 2207/20048* (2013.01); *G06T 2207/30164* (2013.01); *G06T 2207/30168* (2013.01)

(58) Field of Classification Search
CPC ......... G06N 3/04; G06N 3/047; G06N 3/0464; G06N 3/049; G06N 3/043; G06N 3/0442; G06N 3/0455; G06N 3/0475; G06N 3/048; G06N 3/0495; G06N 3/086; G06N 3/0895; G06N 3/09; G06N 3/092; G06N 3/091; G05B 2219/36252; G05B 19/4097; G05B 19/18; G05B 19/4183; G05B 2219/45165; G05B 2219/36175; G05B 2219/45212; G05B 2219/50064; G05B 19/182; G05B 19/4069; G05B 19/409; G05B 19/40937; G05B 19/414; G05B 13/0265; G05B 13/027; G05B 11/00; G05B 13/042; G05B 13/00; G05B 13/0205; G05B 13/021; G05B 15/00; G05B 2219/32015; G05B 23/0281; G05B 13/02; G05B 2219/31048; G05B 2219/45122; G05B 2219/45041; G05B 2219/45138; G05B 2219/45139; G05B 2219/45154; G05B 2219/45163; G05B 2219/45164; G05B 2219/45188; G05B 2219/31077; G05B 2219/21072; G05B 2219/4719; G05B 2219/49012; G05B 2219/49013; G05B 2219/49018; G05B 2219/49027; G05B 2219/49031; G05B 2219/49325; G05B 2219/49326; G05B 2219/49328; G05B 2219/49331; G05B 2219/49353; G05B 2219/49371; G05B 2219/50245; G05B 2219/35247; G05B 2219/33198; G05B 2219/36199; G05B 2219/36241; G05B 2219/36415; G05B 2219/37275; G05B 2219/37281; G05B 2219/37288; G05B 2219/37304; G05B 2219/37571; G05B 2219/39033; G05B 2219/40001; G05B 2219/40103; G05B 2219/40416; G05B 2219/40574; G05B 2219/40588; G05B 2219/40613; G05B 2219/40623; G05B 2219/36285; B23K 26/00; B23K 26/032; B23K 26/034; B23K 26/03; B23K 26/0342; B23K 26/0344; B23K 26/02; B23K 26/38; B23K 26/142; B23K 26/062; B23K 26/0823; B23K 26/042; B23K 26/043; B23K 26/046; B23K 26/083; B23K 26/0853; B23K 26/53; B23K 37/0217; B23K 37/0223; B23K 37/0229; B23K 26/0861; B23K 26/103; B23K 26/106; B23K 26/16; B23K 26/0665; B23K 26/048; B23K 26/037; B23K 26/0619; B23K 26/362; B23K 26/364; B23K 26/064; B23K 26/1435; B23K 26/123; B23K 26/126; B23K 26/125; B23K 26/50; B23K 26/707; B23K 15/00; B23K 15/0013; B23K 15/002; B23K 15/08; B23K 15/02; B23K 26/06; B23K 26/0096; B23K 26/067; B23K 26/08; B23K 26/361; B23K 26/55; B23K 26/57; B23K 26/0626; B23K 26/359; B23K 1/0056; B23K 9/1274; B23K 26/0006; B23K 26/009; B23K 26/0093; B23K 26/035; B23K 26/04; B23K 26/044; B23K 26/0604; B23K 26/0608; B23K 26/0613; B23K 26/0622; B23K 26/0643; B23K 26/0648; B23K 26/0652; B23K 26/066; B23K 26/0661; B23K 26/0673; B23K 26/0676; B23K 26/073; B23K 26/0732; B23K 26/0736; B23K 26/0734; B23K 26/0738; B23K 26/082; B23K 26/0821; B23K 26/0617; B23K 26/0624; B23K 26/0838; B23K 26/0846; B23K 26/0876; B23K 26/0869; B23K 26/0884; B23K 26/0892; B23K 26/10; B23K 26/12; B23K 26/122; B23K 26/1224; B23K 26/127; B23K 26/128; B23K 26/14; B23K 26/1423; B23K 26/1436; B23K 26/1437; B23K 26/1438; B23K 26/144; B23K 26/146; B23K 26/1462; B23K 26/1464; B23K 26/147; B23K 26/1476; B23K 26/1482; B23K 26/1488; B23K 26/1494; B23K 26/18; B23K 26/20; B23K 26/206; B23K 26/21; B23K 26/22; B23K 26/211; B23K 26/24; B23K 26/242; B23K 26/26; B23K 26/244; B23K 26/28; B23K 26/30; B23K 26/282; B23K 26/262; B23K 26/302; B23K 26/32; B23K 26/322; B23K 26/323; B23K 26/324; B23K 26/34; G06T 7/0004; G06T 2207/20081; G06T 2207/30164; G06T 7/11; G06T 2207/30168; G06T 2207/20048; G06T 2207/20084; G06T 2207/30136; G06T 7/13; G06T 2207/30108; G06T 7/12; G06T 7/0002; G06T 7/10; G06T 7/194; G06T 5/73; G06T 7/97; G06T 7/521; G06T 1/0014; G06T 7/42; G06T 7/571; G06T 7/80; G06T 2200/24; G06T 2207/10148; G06T 2207/20056; G06T 2207/20112; G06T 2207/20104; G06T 7/001; G06T 7/0008; G06T 7/0006; G06T 7/136; G06T 7/181; G06T 7/149; G06T 7/143; G06T 7/155; G06T 7/162; G06T 7/168; G06T 7/174; G06T 7/187; G06T 5/75; G06T 5/00; G06T 5/90; G06T 5/92; G06T 5/94; G06T 2207/20092; G06T 2207/20101; G06T 2207/20096; G06T 2207/20108; G06T 2207/20152; G06T 2207/20128; G06T 2207/20116; G06T 2207/20121; G06T 2207/20124; G06T 2207/20132; G06T 2207/20156; G06T 2207/20161; G06T 2207/20164; G06T 2207/20168; G06T 2207/20192; Y10S 706/904; Y10S 706/903; Y10S 977/951; G06V 10/82; G06V 20/695; G06V 10/454; G06V 10/25; G06V 10/26; G06V 10/267; G06V 10/273; G06V 10/225; G06V 10/945; G06V 10/24; G06V 10/44; H04L 67/125; B25J 9/1697; B29C 2043/406; B29C 2793/00; B29C 2793/0027; B29C 2793/0009; B29C 43/40; B29C 48/0022; B29C 66/02241; B29C 66/0246; B29C 2793/0036; B29C 2049/5848; B29C 66/0326; B29C 69/001; B29C 69/005; B29C 69/003; B29C 69/002; B29C 2793/0063; B29C 2793/0054; B29C 2793/0018; G05D 2101/15; G01N 15/1433; G01N 2015/1452; G01N 2001/284; G01N 2001/2873; G01N 2001/2886; A61B 18/20; A61B 2018/00601; A61B 3/022; G06F 3/048; G06F 3/0482; G06F 3/04842; G06F 3/0484; G06F 3/01; G06F 3/04847; G06F 3/14; G06F 3/0481; G06F 3/1462; G06F 3/1415; G06F 3/147; H04N 23/631; H04N 23/632; H04N 1/00748; H04N 1/58; H04N 23/67; H04N 23/62; H04N 21/4854; H04N 23/675; H04N 23/676; A61F 9/0084; A61F 9/008; A61F 9/00823; A61F 9/00814; A61F 2009/00853; A61F 2009/00855

See application file for complete search history.

(56) References Cited

U.S. PATENT DOCUMENTS

| | | | |
|---|---|---|---|
| 2004/0034599 A1 | 2/2004 | Ferrero | |
| 2006/0049158 A1 | 3/2006 | Schurmann et al. | |
| 2009/0290014 A1* | 11/2009 | Takata | G06F 1/1626 348/61 |
| 2011/0177952 A1* | 7/2011 | Maher | H10N 60/0576 427/63 |
| 2012/0188365 A1 | 7/2012 | Stork | |
| 2015/0142154 A1* | 5/2015 | Tiano | G05B 19/4065 700/109 |
| 2016/0042499 A1 | 2/2016 | Dhanantwari et al. | |
| 2018/0082416 A1 | 3/2018 | Arulesan et al. | |
| 2019/0005356 A1 | 1/2019 | Tsunoda et al. | |
| 2019/0019728 A1 | 1/2019 | Fitzgerald | |
| 2021/0379729 A1* | 12/2021 | Erichsen | B24C 1/045 |

FOREIGN PATENT DOCUMENTS

| | | | | |
|---|---|---|---|---|
| CN | 105787930 A | * | 7/2016 | |
| CN | 105809704 A | | 7/2016 | |
| CN | 107309545 A | | 11/2017 | |
| CN | 107322397 A | | 11/2017 | |
| CN | 108628061 A | | 10/2018 | |
| CN | 108701650 A | | 10/2018 | |
| CN | 108747029 A | | 11/2018 | |
| DE | 102009031166 A1 | | 9/2010 | |
| DE | 102017219424 A1 | | 5/2019 | |
| EP | 3301642 A1 | | 4/2018 | |
| GB | 1510299 A | | 5/1978 | |
| JP | H11129083 A | | 5/1999 | |
| JP | 2012533434 A | | 12/2012 | |
| JP | 2016078063 A | | 5/2016 | |
| JP | 2021166229 A | * | 10/2021 | B23K 26/032 |

OTHER PUBLICATIONS

Xu et al., RGB-D-Based Pose Estimation of Workpieces with Semantic Segmentation and Point Cloud Registration, Apr. 19, 2019 [retrieved Mar. 22, 2024], Sensors 2019, vol. 19, Issue: 8, 21 pages. Retrieved: https://www.mdpi.com/1424-8220/19/8/1873 (Year: 2019).*

Lin et al., The Study on Machine Tools with Precision Duplication Performance, Apr. 15, 2021 [STIC request retrieved: Mar. 21, 2024], Advanced Science Letters, vol. 8, pp. 37-42. (Year: 2012).*

Search machine translation of JP-2021 1166229-A to Tsuyoshi et al., Inspection Device and Inspection Method, translated Aug. 22, 2024, 34 pages. (Year: 2024).*

Perminov et al., Automated image analysis for evaluation of wafer backside chipping, Aug. 30, 2018 [retrieved Aug. 22, 2024], The International Journal of Advanced Manufacturing Technology, vol. 99, pp. 2015-2023. Retrieved: https://link.springer.com/article/10.1007/s00170-018-2647-9 (Year: 2018).*

* cited by examiner

METHOD FOR EVALUATING A LASER CUT EDGE, MOBILE TERMINAL AND SYSTEM

CROSS REFERENCE TO RELATED APPLICATIONS

This application is a continuation of International Application No. PCT/EP2020/063545 (WO 2020/259920 A1), filed on May 14, 2020, and claims benefit to German Patent Application No. DE 10 2019 209 088.5, filed on Jun. 24, 2019. The aforementioned applications are hereby incorporated by reference herein.

FIELD

The disclosure relates to a method for evaluating a laser cut edge, to a mobile terminal and to a system for carrying out steps of the method.

BACKGROUND

Laser cutting, also called laser beam cutting, denotes the severing of solids by means of continuous or pulsed laser radiation by way of material ablation. Metals, plastics, glass and organic materials can be cut in this way. In this case, the parameters of the laser radiation, such as wavelength, average power, pulse energy and pulse duration, have to be adapted according to the application. In addition, a cutting nozzle often arranged concentrically with respect to the laser provides a process gas which protects the focusing optical unit against vapors and spatter and furthermore drives the removed material from the kerf. The cut edge can arise in a highly varied manner in particular when cutting metal, in particular sheetmetal. Different states of matter of the kerf material are established depending on the type of process gas supplied and the temperature reached in the active region. A high cut quality is characterized by little striation on the cut edges and the absence of burring on the underside of the cut. The continuous feed and the resulting melting of the material can bring about the solidification of the material on the cut edges. In this case, the solidification may take place in an undulatory fashion, which may be accompanied by a characteristic striated structure or the roughness of the cut. Dross formation or burring is often ascribed to an excessively low driving force of the gas flow. Molten drops on the lower edge of the cut may solidify and form dross/burr adhering to a greater or lesser extent. The parameters that influence the cut quality include, inter alia, the focus position, the feed speed, the laser power, the intensity distribution or else the cutting gas pressure. A cut edge is often evaluated by viewing or manual feeling on the part of worker or by measurement of a height profile using an expensive measurement sensor system. Depending on the subsequent use of the cut workpiece, highly varied, in some instances also very stringent, requirements are made of the cut edge quality.

US 2006/0049158 A1 specifies a method for controlling an automatic laser process in which the result of the process is recorded by a camera and used for the further control of the process.

SUMMARY

In an embodiment, the present disclosure provides a method for evaluating a laser cut edge of a workpiece. The method includes capturing image data of the laser cut edge and its surroundings, segmenting the image data, and identifying a segment of interest of the image data. The segment of interest comprises image data of the laser cut edge. The method further includes carrying out an image quality detection for the segment of interest and generating, based on the image quality detection, an output for a user.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

The present disclosure provides for improving the quality during the evaluation of a laser cut edge.

A method according to the present disclosure for evaluating a laser cut edge of a workpiece comprises at least the following steps:
A) capturing image data of the laser cut edge and its surroundings;
B) segmentation of the image data and identification of a segment of interest of the image data, wherein the segment of interest comprises image data of the laser cut edge;
C) carrying out an image quality detection for the segment of interest;
D) generating an output for a user, on the basis of the image quality detection.

The workpiece preferably consists of solid material, in particular of highly reflective material, such as e.g. glass or metal, in particular sheetmetal.

In the present method, in step A), an image of the laser cut edge and its surroundings is captured by means of a camera. In digitized form, the captured image is stored as image data in an image file. In this case, a pixel is a single image point of an image. It is possible for the image exert captured by the camera to comprise regions which do not concern the laser cut edge, but rather are at distance from the laser cut edge on the workpiece or even outside the workpiece. These so-called surroundings of the laser cut edge are less relevant to the assessment of the image quality than the image exert directly concerning the laser cut edge.

The segmentation of the image data in step B) is effected by means of electronic image processing and results in the identification of a segment of interest of the image, wherein the segment of interest of the image comprises image data of the laser cut edge. For good functioning of the method, the segment of interest should quite predominantly comprise image data of the laser cut edge and only quite a small portion of the segment of interest should comprise image data of the surroundings of the laser cut edge.

Preferably, step B) involves determining, for each pixel of the image data, whether the pixel is part of the laser cut edge or is part of the surroundings of the laser cut edge. With further preference, for each pixel of the image data, the fact of whether said pixel is part of the laser cut edge or part of the surrounds of the laser cut edge is stored as the result of step B).

In one embodiment, step B) is performed by means of a neural network. The neural network, also called artificial neural network, is an algorithm that is usually operated on a computer. It has an input layer and an output layer and optionally one or more intermediate layers and can be trained, e.g. by means of "deep learning". In the input layer, data, e.g. image data, can be fed to the neural network. In the output layer, the neural network can output proposals for a result, e.g. proposals for the segmentation of the image data. The neural network can additionally provide each of said proposals with a value that outputs the probability with which the algorithm evaluates the segmentation as having been carried out successfully. The correctness of the output data can then be evaluated by a user. The neural network can use this evaluation by a user in order to improve its algorithm or its algorithms. To that end, in the intermediate layer(s), it is possible to interlink the data of the input layer with factors or computation functions with other data and thus to generate new data in an intermediate layer. The other data can be data of this or a further intermediate layer or of the output layer. This adaptation of the factors or computation functions can be referred to as "training" of the neural network. The training of the neural network enables the latter to learn from past experiences. In a training phase of the neural network, it is also possible to use exemplary images from a training database which depict laser cut edges against a (for example single-colored, in particular green) background. For these exemplary images, a label can be added to the pixels by means of image processing, said label indicating which pixel belongs to the laser cut edge and which to the (for example green) background. The collection of these labels and the associated pixels is referred to as "ground truth" of the associated exemplary image. Furthermore, the green background can be replaced by other backgrounds and real recording scenarios can thus be simulated. The training database can thereby be enlarged.

In one embodiment, a combination of a "spatial pyramid pooling" algorithm with an "encoder decoder algorithm" is used for detecting the segment of interest. Preferably, the two algorithms are combined such that the encoder module contains diverse semantic information and detailed object boundaries, e.g. boundaries of the laser cut edge, are obtained by a simple and effective decoder module. The encoder module allows features to be extracted with arbitrary resolution by means of an "atrous convolution" algorithm. One example of a suitable algorithm is the DeepLabV3+ network, as described e.g. in Chen, L.-C., Zhu, Y., Papandreou, G., Schroff, F., Adam, H., "Encoder-Decoder with Atrous Separable Convolution for Semantic Image Segmentation" (arXiv:1802.02611v3 [cs.CV] 22 Aug. 2018).

Step C) involves carrying out an image quality detection of the segment of interest. In this case, the image quality detection is restricted to the segment of interest since the latter primarily represents the laser cut edge. The image quality detection for the surroundings of the laser cut edge, i.e. the regions of the image which do not represent the laser cut edge, is of less relevance to the evaluation of the quality of laser cut edges.

Step C) preferably comprises one or more aspects of image quality, e.g. an exposure detection and/or a sharpness detection.

For the sharpness detection, the image data of the image are preferably transformed into the frequency domain. The transformation into the frequency domain can be effected e.g. by means of a Fourier transformation. The sharpness detection is then preferably effected on the basis of the image data in the frequency domain. In one embodiment, for the sharpness detection in the frequency domain, use is made of an algorithm which works solely with the recorded image data in the segment of interest, i.e. does not require a comparison image with good or satisfactory sharpness. One example of a suitable algorithm is an NRIQA method, as described e.g. in De, K., Masilamani, V., "Image Sharpness Measure for Blurred Images in Frequency Domain" (Procedia Engineering 64 (2013) 149-158).

The method can enable a user to record an image of the laser cut edge which, in terms of the quality, is sufficient to determine the quality of the cut edge itself. In step D), in this case, the user obtains for example feedback with regard to the setting of best possible parameters for the camera and/or the optimization of e.g.:

Sharpness in the 3 dimensions, stationary best possible contrast ratio, motion blur;

Illumination intensity: avoidance of over- and underexposure and application of HDR methods (High Dynamic Range) for expanding the maximum dynamic range;

Noise: optimization of ISO parameterization;

Gamma correction: automatic parameter adaptation to ambient light, e.g. daylight, neon lamp, etc., for realistic color rendering;

Aperture: adaptation to highest possible depth of field

The determination of the quality of the cut edge itself can then be effected in a step E) of the method for example by means of the viewing of the image of the laser cut edge and/or by machine by means of image processing.

In one embodiment of the method, before step A), the laser cut edge is cut by means of a laser beam and in particular using a compressed air jet. This laser cutting is preferably carried out by means of a laser cutting machine. Preferably, the result of the evaluation of the quality of the laser cut edge is fed back to the laser cutting machine and can thus influence future cutting processes.

In one embodiment of the method, before step A), parameters concerning the laser cut edge and/or the workpiece are received. The reception can be effected for example by means of an input by the user. The reception can also be effected by means of the reception of data from the laser cutting machine or from a superordinate controller. In addition, e.g. an identifier of the workpiece or the shape of the workpiece can be captured by the camera and a proposal for parameters can be displayed to the user.

The image data are recorded by means of a camera. The camera is an image recording apparatus, in particular in the visible range. A camera can also be a system comprising a plurality of recording devices and an image processing component, which generates an overall image from the plurality of images. The camera is preferably configured to output image data in digital form.

A mobile terminal having a camera configured to capture image data of a laser cut edge with surroundings can be used when carrying out the method.

The mobile terminal is configured to communicate the image data to a computing unit and to receive image data from the computing unit, wherein the received image data are segmented and a segment of interest is identified in the received image data, wherein the segment of interest comprises image data of the laser cut edge; and wherein the received image data comprise the result of an image quality detection for the segment of interest. The mobile terminal is thus configured to receive image data which are processed in accordance with steps B) and C) of the method in a computing unit.

In this case, the computing unit can be arranged for example in the laser cutting machine or can be arranged for example in a superordinate control unit of a superordinate controller. This can be the case for example if the mobile terminal is embodied as a webcam.

In one embodiment, the computing unit in which steps B) and C) of the method are performed can also be arranged in the mobile terminal. This can be the case for example if the mobile terminal is embodied as a cellular phone or tablet computer.

In one embodiment, the mobile terminal can comprise an output interface configured to generate an output for a user, wherein the output is based on the result of the image quality detection. Such an output interface is present in the mobile terminal, for example, if the latter is embodied as a cellular phone. The user can then record an image of the laser cut edge using the camera of the cellular phone and, via the same cellular phone, acquires feedback as to whether the quality of the image is sufficient and what parameters, e.g. image exert, illumination, etc., still need to be changed by the user in order to obtain a better image quality during the next recording.

In one embodiment, the mobile terminal comprises at least one interface for receiving parameters concerning the laser cut edge and/or the workpiece. The parameters are preferably received before step A) of the method. The reception can be effected for example by means of an input by the user via an input interface. The reception can also be effected by means of the reception of data from the laser cutting machine or from a superordinate controller, e.g. via a wireless communication interface.

Steps of the method can proceed on elements of a system. In this case, the system can comprise a laser cutting machine and a mobile terminal. In this case, the laser cutting machine can be configured to cut a laser cut edge into a workpiece by means of a laser beam and in particular additionally by means of a compressed air jet. The mobile terminal can be embodied as described above.

The described method, the described mobile terminal and the described system can make it possible to achieve the highest possible image quality in relevant image regions by means of the processing of image data and targeted feedback to the user. The highest possible image quality achievable can then be a good basis for a further step E) for evaluating the quality of a recorded object, e.g. a laser cut edge. The evaluation in step E) can then be effected manually or in an automated manner. The described method likewise makes it possible to use e.g. a smartphone for recording the laser cut edge. The method affords the advantage that the user is assisted in recording a good quality image of the laser cut edge, even if the autofocus of the smartphone e.g. does not focus on the laser cut edge, which, under certain circumstances, occupies only a small portion of the image, or if the user cannot hold the smartphone completely steady in his/her hand. The feedback gives the user the option to repeat the recording.

In one embodiment, a computer-readable, in particular nonvolatile, in particular tangible, storage medium is provided, encoded with processor-readable instructions for carrying out steps of the method for evaluating a laser cut edge.

Further advantages of the disclosure are evident from the description and the drawing. Likewise, according to the disclosure, the features mentioned above and those which will also be explained further can each be used individually by themselves or as a plurality in any desired combinations. The embodiments shown and described should not be understood as an exhaustive enumeration, but rather are of exemplary character.

Figure 1:
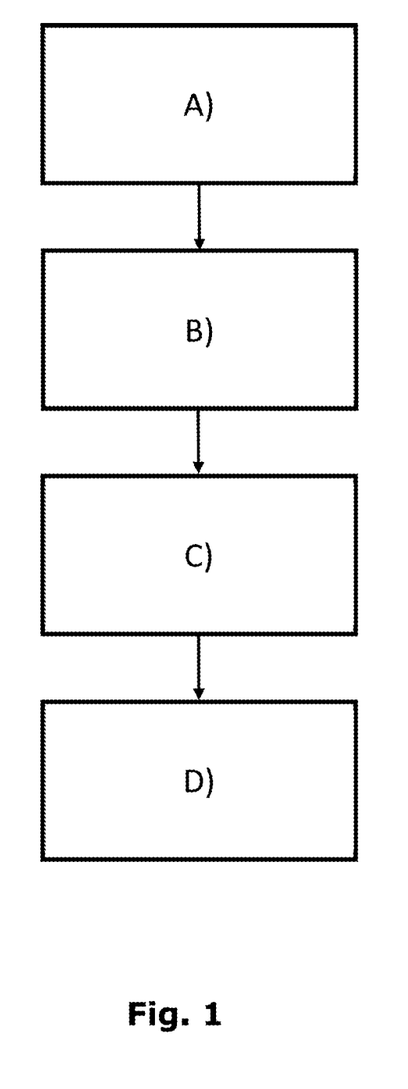
FIG. 1 schematically shows a flow diagram of the method.
Figure 2:
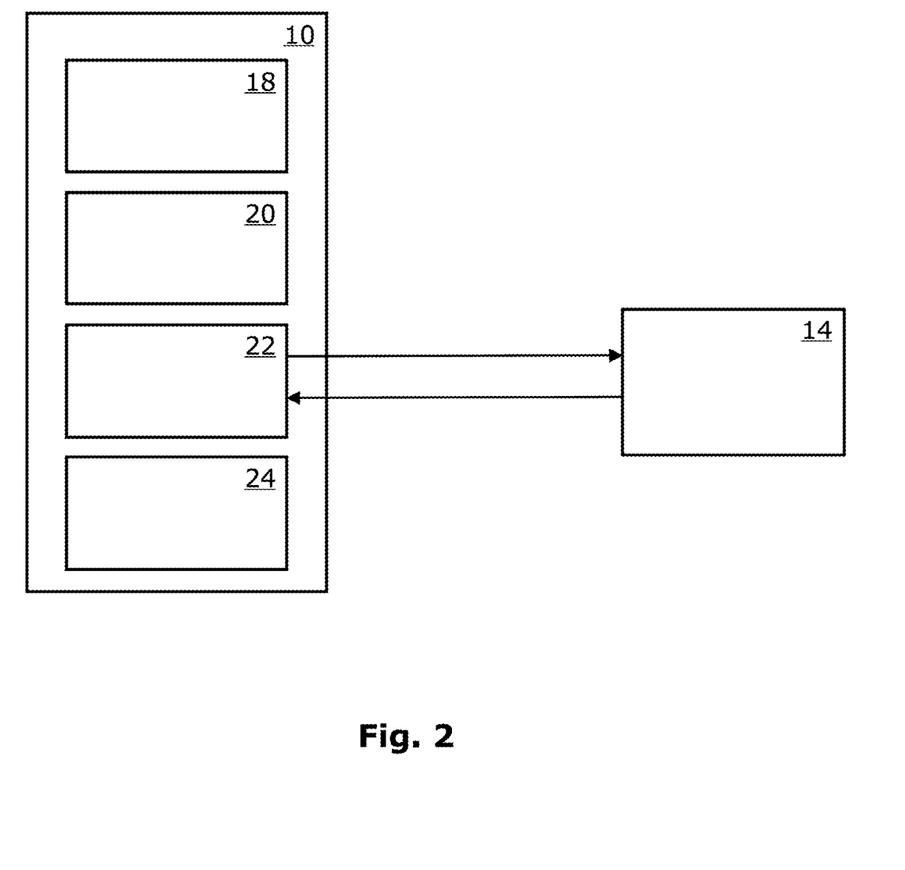
FIG. 2 schematically shows a system with a mobile terminal and a laser cutting machine.

FIG. 1 schematically shows a flow diagram of the method for evaluating a laser cut edge 16 (FIG. 5) of a workpiece 12 (FIG. 5), comprising steps A), B), C) and D). In step A), image data of the laser cut edge 16 and its surroundings are captured by means of a camera 18. In step B), the image data are segmented, in particular by means of a neural network, and a segment of interest of the image data is determined by means of the segmentation. For a method for evaluating the quality of a laser cut edge, the laser cut edge itself is the essential region of the image. During the segmentation of the image data, therefore, the image points, pixels, of the image data which lie on the laser cut edge 16 are assigned to the segment of interest. Further image points, pixels, are assigned to the surroundings of the laser cut edge 16. Step C) then involves carrying out for the segment of interest an image quality detection, in particular image sharpness detection, preferably in the frequency domain. Step D) involves generating an output for a user and outputting it preferably on a screen 24 (FIG. 2). In the output, the user is informed about the result of the image quality detection and can thus obtain an indication as to whether or not the quality of the image is sufficient for a possibly subsequent evaluation of the quality of the laser cut edge 16 in a step E). If the image quality is not sufficient for an evaluation of the quality of the laser cut edge 16, a proposal for repeating the recording of the image can be made to the user. This can be done until enough images, e.g. at least one image, with sufficient quality is/are available.

FIG. 2 schematically shows a system with mobile terminal 10 and laser cutting machine 14. The mobile terminal 10 comprises a camera 18, optionally a keyboard 20 as input interface, a communication interface 22, e.g. for wireless communication, and also a touch-sensitive screen 24. The screen 24 can also be embodied as a screen without a touch-sensitive surface, i.e. not have input functionality. The mobile terminal is configured to communicate with the laser cutting machine 14 or other units via the communication interface 22. This communication is preferably effected wirelessly, but wired communication can also be provided. Via the communication interface 22, the mobile terminal can receive e.g. parameters concerning the laser cut edge 16 and thus the workpiece 12, e.g. from the laser cutting machine 14. Said parameters comprise e.g. data regarding the type of material of the workpiece 12, regarding the type of cutting method and/or regarding the thickness of the workpiece 12.

In one embodiment, via the communication interface 22, the mobile terminal 10 can likewise communicate the image data recorded by the camera 18 to a computing unit and receive image data from the computing unit. The received image data are segmented and the segment of interest is identified in the received image data. The received image data comprise the result of an image quality detection for the segment of interest. The computing unit in turn is configured to segment the image data and to identify a segment of interest of the image data, wherein the segment of interest comprises image data of the laser cut edge; and wherein the computing unit is configured to carry out an image quality detection for the segment of interest. The computing unit mentioned can be realized for example in the computing unit 122 illustrated in FIG. 5.

In a further embodiment, the computing unit is realized within the mobile terminal 10. For this embodiment, the communication between the mobile terminal and the computing unit is effected within the mobile terminal 10.

Figure 3:
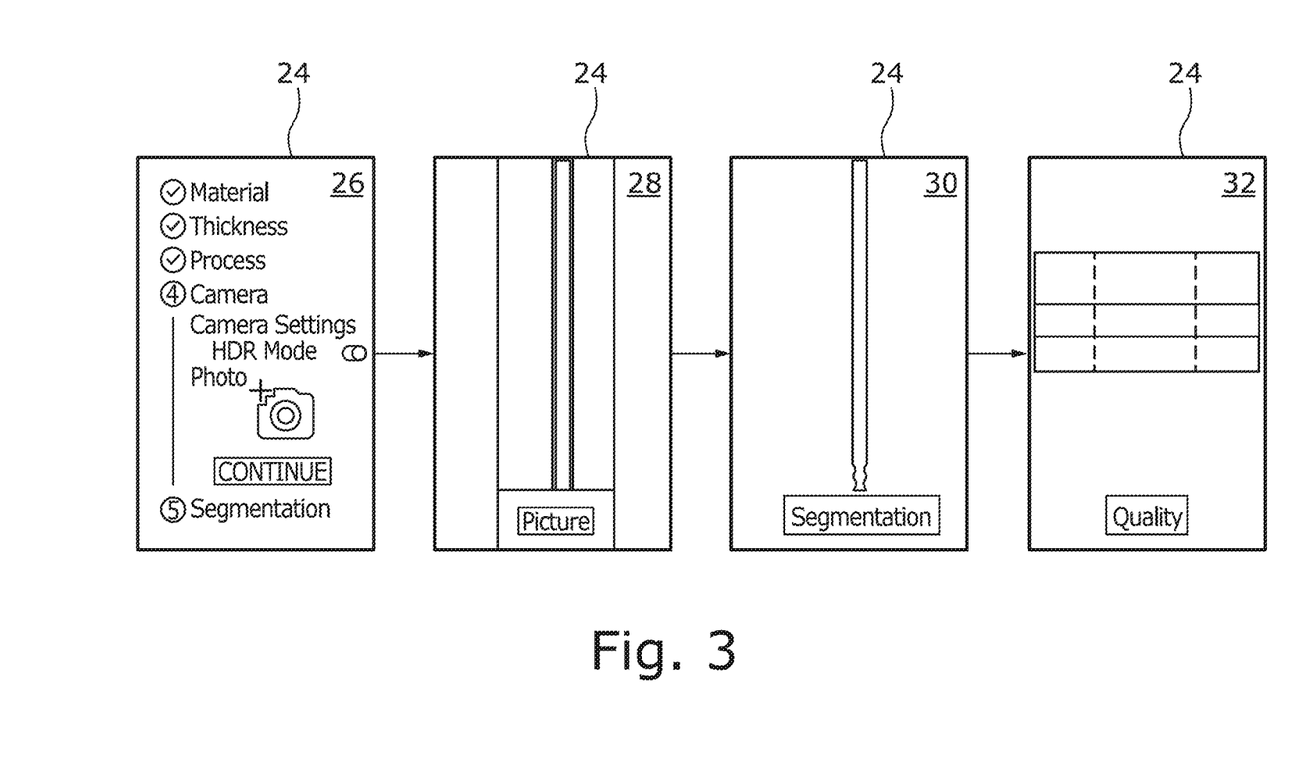
FIG. 3 schematically shows possible displays on the touch-sensitive screen.

FIG. 3 shows schematic possible displays, in particular on the touch-sensitive screen 24, e.g. on a cellular phone or tablet computer. The image (display) 26 displays in exemplary fashion the situation before step A) of the method, in which parameters regarding the material used, regarding the material thickness used and regarding the process used have already been received. This may have been effected for example by means of an input by the user or reception via a communication interface. At the same time image 26 reveals that the camera is ready for recording.

Image (display) 28 displays in exemplary fashion the result of step A) of the method, i.e. the image recorded by the camera is displayed. Image (display) 30 displays in exemplary fashion the result of step B) of the method, i.e. the result of the segmentation is displayed such that the user can identify in which region of the image the method locates the laser cut edge.

Image (display) 32 displays in exemplary fashion the result of steps C) and D) of the method, i.e. the result of the image quality detection is output to the user. The example illustrated involves displaying in different gray shades, in reality preferably in different colors, what the image sharpness is like in the different image regions and whether it is sufficient or whether recording a further photograph is recommended.

Figure 4:
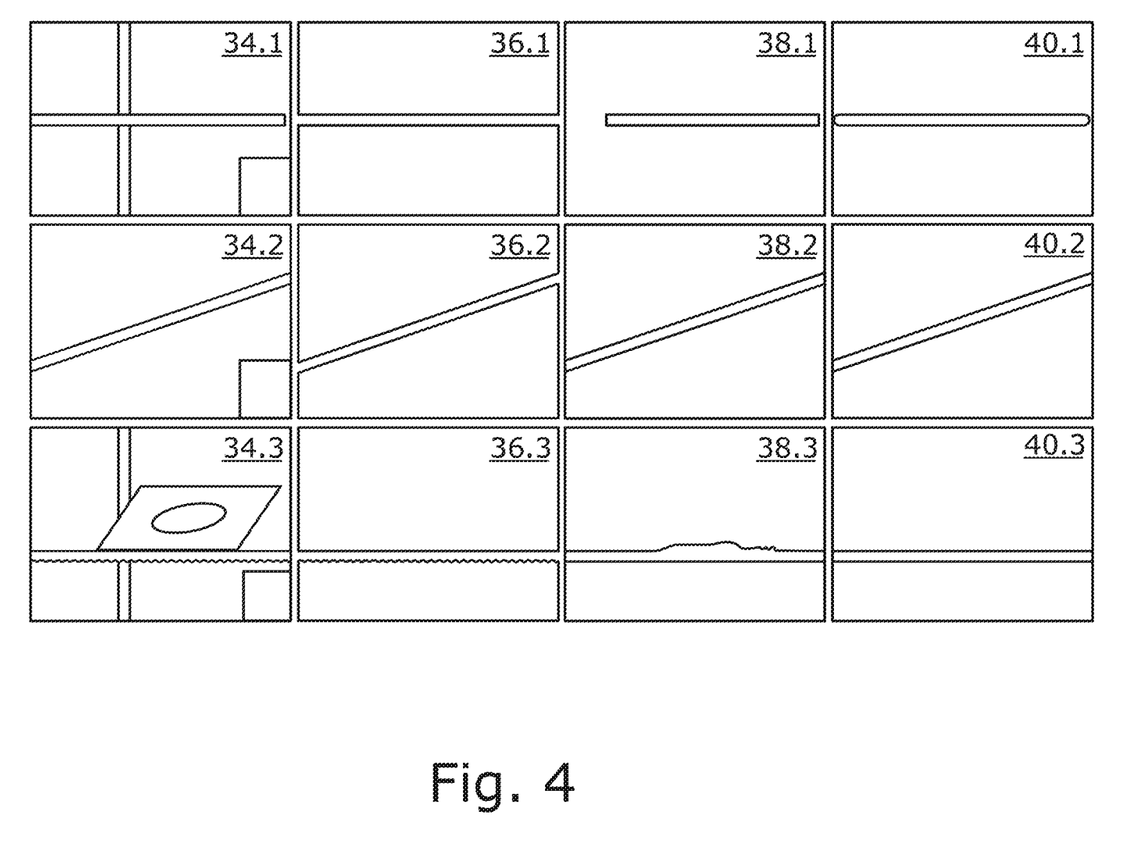
FIG. 4 shows results of segmentations by way of example.

FIG. 4 shows examples of results of segmentations. The images 34.1, 34.2 and 34.3 are exemplary test images of laser cut edges. The images 36.1, 36.2, 36.3 are respectively assigned ground truth data, i.e. the "correct" desired segmentation, in which the cut edge is unambiguously identified. The images 38.1, 38.2, 38.3 show the result of a first segmentation algorithm and the images 40.1, 40.2, 40.3 show the result of a second segmentation algorithm. The images 38.1, 38.2, 38.3, 40.1, 40.2, 40.3 reveal that each of the two algorithms has identified the segment of interest with the laser cut edge—discernible in the more lightly colored region in the respective images 38.1, 38.2, 38.3, 40.1, 40.2, 40.3.

Figure 5:
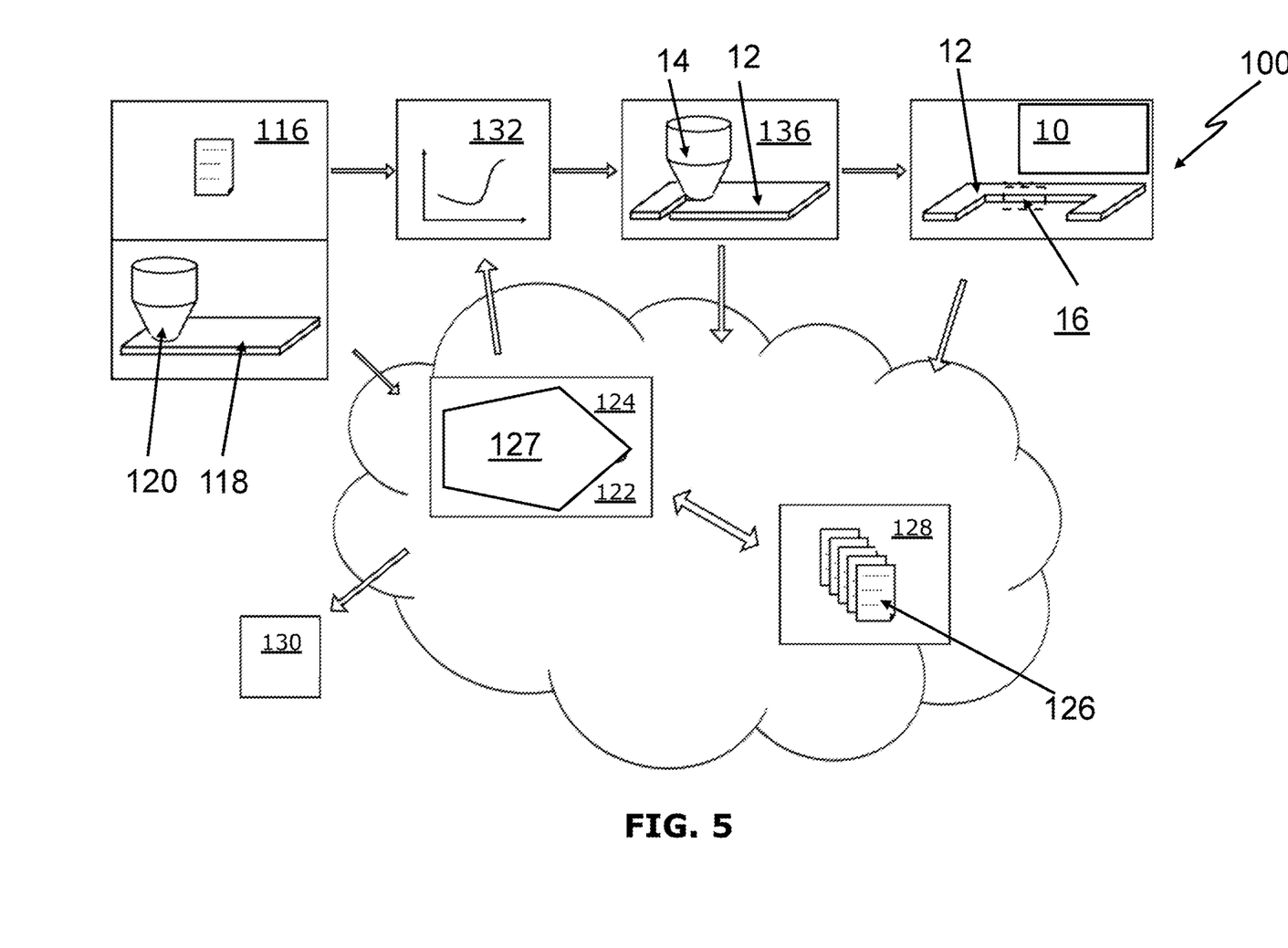
FIG. 5 shows a schematic illustration of one embodiment of a system with a laser cutting machine.

FIG. 5 shows by way of example a system 100 for processing a workpiece 12 with a laser cutting machine 14.

Via an input 116, at least one material parameter 118, which in particular is characteristic of the workpiece material used and/or the thickness thereof, at least one machine parameter 120, which in particular is characteristic of the laser cutting machine 14 used, and also preferably at least one desired cut edge quality feature are input. Furthermore, at least one desired method parameter, in particular laser power, depth of focus, feed speed and/or gas flow rate, can be input via the input unit 116.

The system 100 can be configured to independently determine the material parameter 118 used by means of metrological detection, in particular by means of weight measurement and comparison with stored material characteristic data, and also the workpiece dimensions of the workpiece 12, in particular by means of measurement of the workpiece 12. Furthermore, the system 100 can be configured to independently determine the laser cutting machine 14 used. Such embodiments result in a reduction of the input outlay in advance of workpiece processing by the laser cutting machine 14.

A computing unit 122 having a method parameter algorithm 124 reads in the material parameters 118 and machine parameters 120 that have been input, and also in particular the desired cut edge quality feature and/or the desired method parameters and stores the information in a data set 126 in a database 128. On the basis of the information that has been input, the method parameter algorithm 124 determines the improved, preferably optimal, method parameters and/or the method parameters required for achieving the desired cut edge quality feature.

For this purpose, the method parameter algorithm has a data aggregation routine 127. Preferably, the method parameter algorithm is embodied in the form of the data aggregation routine 127.

The method parameters thus determined are output via the display 130 and/or forwarded to a controller 132 for controlling the laser cutting machine 14. After the improved, preferably optimal, method parameters have been announced, the user can either approve the method parameter recommendation for application or carry out a different setting of the method parameters and start the method process. Afterward, the workpiece 12 is processed by the laser cutting machine 14 and on the basis of the predefined method parameters. The method parameters that are crucial for the processing of the workpiece 12 by the laser cutting machine 14 and also the method parameters proposed by the method parameter algorithm 124 are added to the data set 126 of this workpiece processing.

In order to enable an unambiguous assignment of the workpiece 12 to the data set 126, it is possible to carry out an identification of the workpiece 12 within the process manually or in an automated manner, in particular by means of laser engraving, preferably of a QR code, in particular during the laser cutting process. Such an identification additionally has the advantage of an automated assignment of the workpiece by means of simple scanning of the workpiece 12 in the further course of the process. If a corresponding identification of the workpiece 12 is carried out, corresponding information is added to the data set 126 of this workpiece processing.

After the processing of the workpiece 12, the quality of the cut edge produced, in particular the various cut edge quality features, are determined. This can be done using the method comprising steps A), B), C) and D). By means of step D), the fact of whether the quality of the optical recording of the cut edge 16 is good enough or whether the user ought to repeat the recording process is indicated to said user. The image data representing the quality of the cut edge 16 are added to the data set 126 of this workpiece processing. Preferably, after the processing of the workpiece 12 by the laser cutting machine 14, an objective determination of the cut edge quality features is carried out in a step E) of the method. In this case, on the basis of the image data, the quality of the cut edge 16 is determined in an automated manner by means of an image processing method in step E). The measurement results are preferably added to the corresponding data set 126 of the workpiece processing.

The database 128 is configured to store all data sets 126 of workpiece processings. The database 128 thus forms the basis for the alteration, in particular improvement, preferably optimization, of the method parameter algorithm 124.

Preferably, workpieces 12 that have already been processed are evaluated with regard to their cut edge quality features and are used for method improvement with regard to the processing of subsequent workpieces 12.

Non-steady-state method parameters 136 measured during laser cutting, for example by means of sensors, can likewise be stored in the database 128 and can supplement the data set 126 of the current workpiece processing. This affords the advantage, in particular, of determining fluctuations in the method parameters during laser cutting and including them in an evaluation of the cut edge quality. As a result, it is possible to achieve a particularly high predictability with regard to the cut edge quality and the machine state.

An alteration, in particular improvement, preferably optimization, of the at least one, in particular all, data aggregation routine(s) 127 of the method parameter algorithm 124 can be effected on the basis of stored data sets 126 in the database 128. In this case, data sets 126 of different users of the system 100 can also be utilized jointly in order to determine an improved, in particular optimal, relationship between input and output parameters of the at least one data aggregation routine 127.

Figure 6:
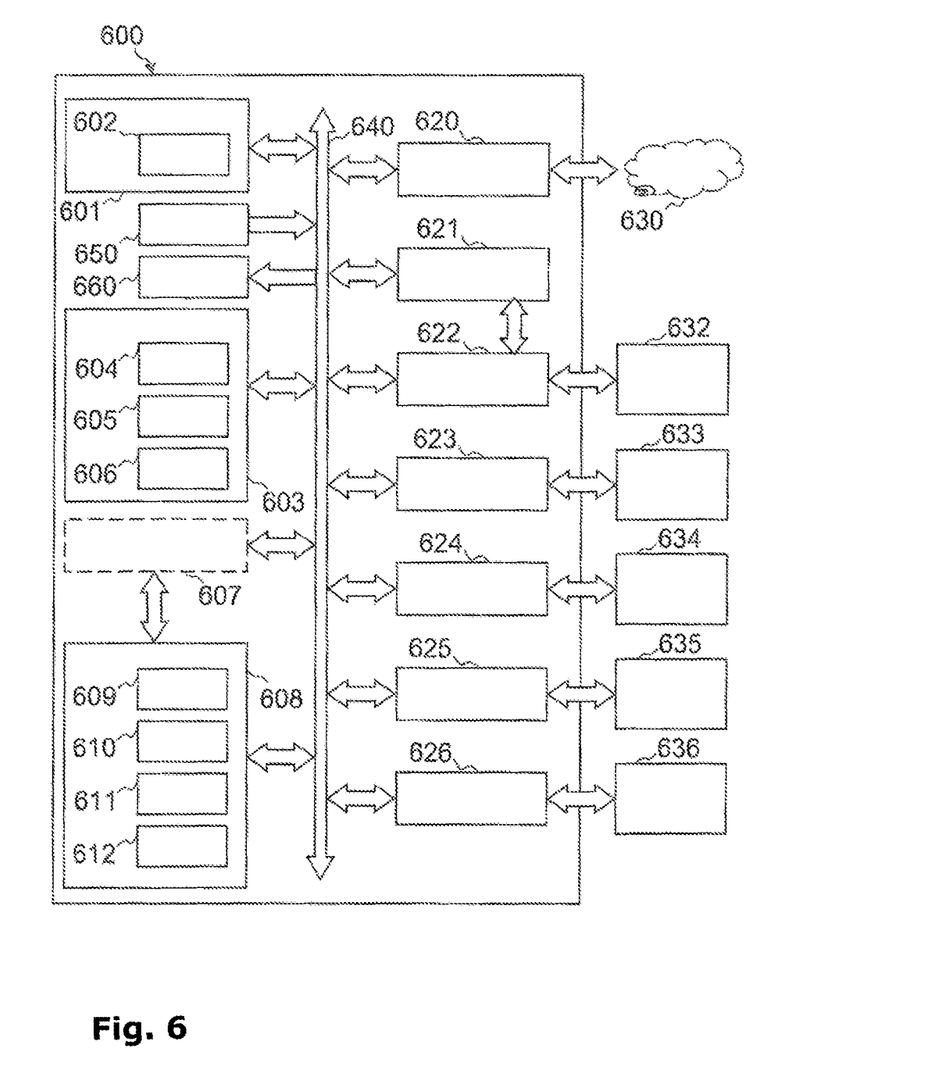
FIG. 6 shows a schematic illustration of one embodiment of a control system.

FIG. 6 shows a schematic illustration of one embodiment of a control system 600 suitable for implementing instructions for implementing one or more aspects of the method in a device. The components should be understood as examples and do not restrict the scope of the use or functionality of hardware, software, firmware, embedded logic components, or a combination of a plurality of such components for implementing specific embodiments. Some or all of the components illustrated can be a part of the control system 600.

In this embodiment, the control system 600 contains at least one processor 601 such as, for example, a central processing unit (CPU, DSP) or a programmable logic device (PLD, FPGA). The control system 600 can also comprise a main memory 603 and a data memory 608, which both communicate with one another and with other components via a bus 640. The bus 640 can also connect a display 632, one or more input devices 633, one or more output devices 634, one or more storage devices 635 and various storage media 636 to one another and to one or more devices of the processor 601, to the main memory 603 and to the data memory 608. All of these elements can be coupled to the bus 640 directly or via one or more interfaces 622, 623, 624, 625, 626 or adapters.

The control system 600 can have any suitable physical form, including, but not limited to, one or more integrated circuits (ICs), printed circuit boards (PCBs), mobile terminals, laptop or notebook computers, distributed computer systems, computational grids or servers. The processor 601 or a central processing unit (CPU) optionally contains a cache storage unit 602 for temporary local storage of instructions, data or processor addresses. The processor 601 is configured to support the execution of the instructions stored on at least one storage medium.

The main memory 603 and the data memory 608 can each be embodied as a computer-readable, in particular nonvolatile, in particular tangible, storage medium. They can comprise various components, including, but should not be limited to, a random access memory component, e.g. RAM 604, in particular a static RAM "SRAM", a dynamic RAM "DRAM", etc., a read only component, e.g. ROM 605, and any desired combinations thereof. The ROM 605 can also function for communicating data and instructions unidirectionally to the processor(s) 601, and the RAM 604 can also function for communicating data and instructions bidirectionally to the processor(s) 601.

The memories 603, 608 and storage media can be connected bidirectionally to the processor(s) 601, optionally by means of a memory control unit 607. Both memories 608, 603 can be used to store the operating system 609, programs 610, data 611, applications 612, application programs, and the like. Often, but not always, the memories 603, 608 are supported by a secondary storage medium (such as a hard disk), which is slower than the primary memory (e.g. memory 603). The memory 603, 608 can e.g. also comprise a magnetic, an optical or a transistorized, a solid-state storage device (e.g. flash-based systems) or a combination of any desired elements from among those mentioned above.

The bus 640 connects a multiplicity of subsystems. The bus 640 can be any one of a plurality of types of bus structures, e.g. a memory bus, a memory controller, a peripheral bus, a local bus, and all combinations thereof, using a multiplicity of bus architectures. Information and data can also be displayed by way of a display 632. Examples of a display 632 include, but are not restricted to, a liquid crystal display (LCD), an organic liquid crystal display (OLED), a cathode ray tube (CRT), a plasma display, and any desired combinations thereof. The display 632 can be connected to processor(s) 601, memories 603, 608, input devices 633, and further components via the bus 640.

The bus 640 can connect all components mentioned above to an external network 630 by way of a network interface 620. Said network can be e.g. a LAN, WLAN, etc. It can establish a connection to further storage media, servers, printers, display devices. It can have access to telecommunications devices and the Internet. The bus 640 can connect all components mentioned above to a graphics controller 621 and a graphics interface 622, which is connectable to at least one input device 633.

The bus 640 can connect all components mentioned above to an input interface 623, which is connectable to at least one input device 633. An input device can include e.g. a keypad, a keyboard, a mouse, a stylus, a touchscreen, etc.

The bus 640 can connect all components mentioned above to an output interface 624, which is connectable to at least one output device 634. An output device 634 can comprise a luminous display, an LED display, a display, e.g. LCD, OLED etc., or an interface to such a facility.

The bus 640 can connect all components mentioned above to a storage access interface 625, which is connectable to at least one storage device 635. The bus 640 can connect all components mentioned above to a further storage access interface 626, which is connectable to at least one storage medium 636. A storage device 635 or a storage medium 636 can e.g. be a solid-state storage element, a magnetic storage element or an optical storage element, in particular comprise a nonvolatile memory. The storage medium can be disconnected from the control system during the operation of the control system, without data being lost. The storage medium can be tangible, i.e. a materially present object.

The bus 640 can be realized wholly or partly by cables or wires (e.g. LAN, RS232etc.) or wholly or partly wirelessly by way of radio connection or the like (e.g. WLAN, WIFI, Bluetooth, NFC etc.).

Display 632, input device 633, output device 634, storage device 635 and/or storage medium 636 can in each case be arranged outside the control system 600 or be integrated therein. They can also be connected to the control system 600 via a connection to the Internet or other network interfaces.

The controller described herein can be realized in such a control system 600. The method steps described herein can be carried out at least partly on such an control system 600.

The computing unit described can be realized in such a processor 601.

The input unit 116 described can be realized in such an input device 633.

The display 24 described can be realized in such a display 632.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for evaluating a laser cut edge of a workpiece, the method comprising:
   A) capturing image data of the laser cut edge and its surroundings, wherein the laser cut edge is formed by laser cutting of the workpiece using a laser cutting machine;
   B) segmenting the image data and identifying a segment of interest of the image data performed by one or more processors, wherein the segment of interest comprises image data of the laser cut edge;
   C) carrying out an image quality detection for the segment of interest performed by the one or more processors, wherein the image quality detection comprises detecting an image sharpness of the segment of interest;
   D) determining by the one or more processors, based on the image quality detection, whether the image sharpness is sufficient;
   E) performing by the one or more processors the following steps:
      upon determining that the image sharpness is not sufficient, generating an output for the user on the output interface, the output recommending recording new image data of the laser cut edge and its surroundings; and
      upon determining that the image sharpness is sufficient, evaluating a quality of the laser cut edge based on the image data of the laser cut edge;
   determining at least one method parameter based on the quality of the laser cut edge; and
   forwarding the at least one method parameter to a controller for controlling the laser cutting machine to perform laser cutting of further workpieces.

2. The method as claimed in claim 1, wherein step B) involves determining and storing, for each respective pixel of the image data, whether the respective pixel represents a part of the laser cut edge.

3. The method as claimed in claim 1, wherein step B) is performed by a neural network.

4. The method as claimed in claim 1, wherein the detecting the image sharpness comprises a transformation of the image data of the segment of interest into a frequency domain, and wherein the detecting the image sharpness is carried out in the frequency domain.

5. The method as claimed in claim 1, further comprising, before step A), receiving one or more material parameters and/or one or more machine parameters concerning the laser cut edge.

6. The method as claimed in claim 5, wherein the one or more material parameters comprises one or more of a type of material of the workpiece or a thickness of the workpiece.

7. The method as claimed in claim 1, wherein the at least one method parameter comprises one of a laser power, a depth of focus, a feed speed, or a gas flow rate of the laser cutting machine.

8. A mobile terminal, comprising:
   a camera configured to capture image data of a laser cut edge with surroundings; and
   a communication interface configured to communicate the image data to a computing unit and to receive an output from the computing unit,
   wherein the computing unit comprises one or more processors configured to:
      segment the image data of the laser cut edge with surroundings and identify a segment of interest, wherein the segment of interest comprises image data of the laser cut edge,
      perform an image quality detection by detecting an image sharpness of the segment of interest,
      generate the output indicating whether the image sharpness is sufficient or recommending capturing new image data of the laser cut edge and the surroundings if the image sharpness is not sufficient;
      evaluate a quality of the laser cut edge based on the image data of the laser cut edge upon determining that the image sharpness is sufficient, and
      determine at least one method parameter based on the quality of the laser cut edge;
   wherein the mobile terminal further comprises an output interface to display the output received from the computing unit, and wherein the communication interface is further configured to forward the at least one method parameter to a controller for controlling the laser cutting machine to perform laser cutting of further workpieces.

9. The mobile terminal as claimed in claim 8, wherein the mobile terminal can be embodied as a cellular phone, tablet computer or webcam.

10. The mobile terminal as claimed in claim 8, further comprising at least one interface for receiving parameters concerning the laser cut edge.

11. The mobile terminal as claimed in claim 10, wherein the at least one interface is embodied as input interface for a user and/or as a communication interface for communication with a laser cutting machine.

12. The mobile terminal as claimed in claim 8, wherein the mobile terminal comprises the computing unit.

13. A system comprising:
a laser cutting machine configured to cut a laser cut edge into a workpiece by a laser beam, and
a mobile terminal as claimed in claim 8.

* * * * *